United States Patent [19]

Meinard et al.

[11] Patent Number: 5,087,456
[45] Date of Patent: Feb. 11, 1992

[54] METHOD OF COMBATTING PESTS BY APPLYING NOVEL GRANULES TO THE SOIL

[75] Inventors: Colette Meinard, Marseille; Jean-Claude Suglia, La Destrousse; Claude Taranta, Aix en Provence, all of France

[73] Assignee: Roussel Uclaf, Paris, France

[21] Appl. No.: 486,798

[22] Filed: Mar. 1, 1990

Related U.S. Application Data

[62] Division of Ser. No. 283,840, Dec. 13, 1988.

[30] Foreign Application Priority Data

Dec. 13, 1987 [FR] France ............................ 87 17634

[51] Int. Cl.$^5$ .................. A01N 25/14; A61K 9/14; A61K 47/32
[52] U.S. Cl. .................. 424/501; 424/409; 71/DIG. 1; 514/521
[58] Field of Search .................. 424/78, 81, 405, 409, 424/489, 501; 71/DIG. 1

[56] References Cited

U.S. PATENT DOCUMENTS

| | | | |
|---|---|---|---|
| 3,329,702 | 7/1967 | Rohr | 71/11 |
| 3,849,105 | 11/1974 | Woods | 71/DIG. 1 |
| 4,134,725 | 1/1979 | Büchel et al. | 71/DIG. 1 |
| 4,343,790 | 8/1982 | Pasarela | 424/81 |

FOREIGN PATENT DOCUMENTS 0201214 11/1986 European Pat. Off. .

Primary Examiner—Thurman K. Page
Assistant Examiner—E. Webman
Attorney, Agent, or Firm—Bierman and Muserlian

[57] ABSTRACT

Granules prepared by absorbing on hydrophilic polymer of acrylic acid polymers and/or acrylamide polymers granules an aqueous emulsion of at least one active principle such as pyrethrinoids and drying the resulting mixture to obtain granules which release the active principle in uniform manner.

4 Claims, No Drawings

METHOD OF COMBATTING PESTS BY APPLYING NOVEL GRANULES TO THE SOIL

PRIOR APPLICATION

This application is a division of U.S. patent application Ser. No. 283,840 filed Dec. 13, 1988, now pending.

STATE OF THE ART

Related prior art includes German Patent Application No. 1,936,748, European Patent Application No. 0,201,214 and U.S. Pat. No. 3,329,702.

OBJECTS OF THE INVENTION

It is an object of the invention to provide novel granules useful in the phytosanitary field and the field of human and animal pharmaceuticals.

This and other objects and advantages of the invention will become obvious from the following detailed description.

THE INVENTION

The novel granules of the invention are prepared by absorbing on hydrophilic polymer granules an aqueous emulsion of at least one active principle and drying the resulting mixture to obtain granules which release the active principle in uniform manner.

The polymers used as the base for the granules are known products and have been used, for example, as water retainers in agriculture, as media for in vitro culture, as media for pregermination of seeds, as separate water reserves for plants, as fertilizer fixatives and as a medium for mushroom culture. Examples of these granules are those sold under the Trade Mark AQUA-SORB ® (acrylic acid, acrylamide copolymer 50/50) such as AQUASORB PR 3005 type A or PR005 type A of 2 to 3 mm granule size, or AQUASORB PR 3005 type B or PR005 type B of 1 mm granule size. Preferred granules are those made up of polymers of acrylic acid or of acrylamide, or of polymers of acrylic acid and acrylamide.

The drying is preferably effected with talc such as LUZENAC talc which acts both as a drying agent and as a lubricant, or any other agent which facilitates the fluidity of the granule.

The granules of the invention have the advantage of a simple and regular release of the active principle such as pesticides as can be seen from the test data infra.

Preferred granules are those prepared with an aqueous emulsion containing a solvent for the active principle(s), water, a cosolvent, a surfactant and a film-forming thickening agent. The amount of water is usually 25 to 60%, preferably 30 to 50% by weight of the composition.

The solvent used should have a low solubility in water, and must be a good solvent for the active material. For example, it can be a phthalate such as dimethyl, diethyl or dibutyl phthalates used on their own or coupled with an aromatic-type solvent.

The surfactant used is generally a phosphoric ester. The phosphoric ester is used in acid form or neutral form and it may be for example acid or neutral alkyl ether phosphates sold under the name AGRIMUL ® DMF 539 or under the name AGRIMUL DMF 395. It may also be phosphoric ester amine salts sold under the name AGRILAN F535 or Agrilan F546 or a phosphoric ester of ethoxylated nonphenol sold under the name BEYCOSTAT Q A.

The cosolvent is preferably a diol such as propanediol. The film forming thickening agent is preferably a resin of polyvinyl alcohols and the film-producing agent used performs simultaneously the double functions of thickening agent and of film-producing agent.

More preferred granules use an aqueous emulsion containing 1 to 5% of active principle, 30 to 50% of water, 10 to 30% of dimethyl phthalate, 0 to 10% of phosphoric ester 5 to 20% of propandiol and 5 to 10% of a polyvinyl alcohol resin.

The active principle(s) are phytosanitary products such as pesticides, herbicides or plant growth regulators.

The pesticides used are preferably pyrethrinoids such as for example deltamethrin or also a product chosen from the group consisting of permethrin, cypermethrin, alphamethrin, tralomethrin, cyhalothrin, fenvalerate, cyfluthrin, flucythrinate, fluvalinate, fenpropathrin, tefluthrin and bifanthrin, as well as other derivatives of cyclopropane carboxylic acid possessing biological properties.

The granules of the invention are interesting, for example for combatting parasites sensitive to the active principles used. They improve the persistency of action and regularity of activity and they are particularly effective in combatting insects, acariens and nematodes.

When used in the phytosanitary domain, the granules of the invention can be spread over the soil with agricultural machines and then mixed into the soil. The granules are then placed under various irrigation systems, either natural (rain), or artificial whereby they will then store up the water. As the soil dries out, the granules will put back this water and as well as the phytosanitary formulation by capillary action. This cycle of successive retentions and releases can be repeated several times. These impregnated granules, which are easy to make, are an ideal type of formulation adapted to the treatment of soil. They offer two advantages, namely an ensured protection of the active material and an availability of the latter.

In the following examples there are described several preferred embodiments to illustrate the invention. However, it is to be understood that the invention is not intended to be limited to the specific embodiments.

EXAMPLE 1

Granules were prepared by mixing a solution containing 30 g of deltamethrin, 270 g of dimethyl phthalate, 50 g of AGRIMUL DMF 539 ® (alkyl ether phosphate) and 5 g of ethylhydroxyethyl cellulose (EHEC) with a solution containing 65 g of MOWIOL 30/88 ®, 160 g of propanediol-1,2,1 g of citric acid and 419 g of softened water. Then, 200 g of water were added to the resulting solution and the suspension obtained was sprayed on to 300 g of Aquasorb granules to obtain a homogeneous absorption of the solution. 120 g of talc were then added to the granules thus obtained, and after mixing the desired granules were obtained.

EXAMPLE 2

Granules at 0.025% were prepared with an aqueous formula containing 30 g of pentafluorobenzyl (1R,cis) 2,2-dimethyl -3-(2-fluoro-3-methoxy-3-oxo-1-(ΔE) propenyl)cyclopropane carboxylate, 270 g of dimethyl phthalate, 50 g of Agrimul DMF 539 ®, 70 g of Mowiol 4/88, 160 g of propanediol-1,2 and 420 g of softened water, 8.6 g of the solution obtained were diluted with 40 g of water and then 73 g of Aquasorb granules were impregnated therewith. 8.8 g of a 25% solution of Beycostat Q in methylene chloride were then sprayed onto the granules, 20 g of talc were added, and after mixing, the granules sought were obtained.

EXAMPLE 3

Granules at 0.8% were prepared using a composition containing 30 g of tefluthrin, 270 g of dimethyl phthalate, 50 g of Agrimul DMF 539 ®, 70 g of Mowiol 4/88, 160 g of propanediol-1,2 and 420 g of softened water, 27 g of this solution were diluted with 40 g of water and then 62 g of Aquasorb granules were impregnated therewith. 8.8 g of a 25% solution of Beycostat Q in methylene chloride were then sprayed onto the granules, 20 g of talc were added, and after mixing the granules sought were obtained.

BIOLOGICAL TEST a) It was found that the granules of Example 1 very clearly improved the persistency of action of deltamethrin on the insect SCOTIA SEGETUM. It was found that at a dose of 0.25 ppm of active principle, 45 days after the start of the treatment, the mortality rate was 45% and that a dose of 1.5 ppm of active principle, the mortality rate was 100%.

b) An excellent activity of the 0.05% deltamethrin granule was also found, whether it be immediate activity or activity after 50 days, with regard both to the SCOTIA SEGETHUM and GRILLUS DOMESTICUS species.

Various modifications of the compositions and method of the invention may be made without departing from the spirit or scope thereof and it is to be understood that the invention is intended to be limited only as defined in the appended claims.

What we claim is:

1. A method of combatting insects in a field comprising applying to the field surface an insecticidally effective amount of the granules prepared by absorbing on hydrophilic polymer granules of at least one member of the group consisting of acrylic acid polymers and acrylamide polymers an aqueous emulsion of 30 to 50% of water, 10 to 30% of dimethyl phthalate, 1 to 5% of active principle, 0 to 10% of phosphoric ester, 5 to 20% of propanediol and 5 to 10% of polyvinyl alcohol resin, all precentages based on the total weight of the emulsion, and drying the resulting mixture to obtain granules which release the active principle in uniform manner, wherein the active ingredient is deltamethrin.

2. The method of claim 1 wherein the granules are made of acrylic acid polymers.

3. The method of claim 1 wherein the granules are made of acrylamide polymers.

4. The method of claim 1 wherein the granules are made of acrylic acid polymers and acrylamide polymers.

* * * * *